US008692675B2

(12) United States Patent
Agrawal et al.

(10) Patent No.: US 8,692,675 B2
(45) Date of Patent: Apr. 8, 2014

(54) VIBRATORY FEEDBACK SYSTEMS AND METHODS

(75) Inventors: Sunil K. Agrawal, Newark, DE (US); Kyle N. Winfree, Paoli, PA (US); David Hilgart, Salt Lake City, UT (US)

(73) Assignee: University of Delaware, Newark, DE (US)

( * ) Notice: Subject to any disclaimer, the term of this patent is extended or adjusted under 35 U.S.C. 154(b) by 267 days.

(21) Appl. No.: 13/307,585

(22) Filed: Nov. 30, 2011

(65) Prior Publication Data

US 2012/0154153 A1    Jun. 21, 2012

Related U.S. Application Data

(60) Provisional application No. 61/418,201, filed on Nov. 30, 2010, provisional application No. 61/419,046, filed on Dec. 2, 2010.

(51) Int. Cl.
*G08B 23/00* (2006.01)
*G08B 21/00* (2006.01)

(52) U.S. Cl.
USPC ............... 340/573.1; 340/573.7; 340/665; 36/136; 601/46; 600/587

(58) Field of Classification Search
USPC ............ 340/573.1, 573.7, 665, 666, 669; 36/136, 141, 145, 153, 1; 601/46, 70, 601/22, 79; 600/587, 592, 595
See application file for complete search history.

(56) References Cited

U.S. PATENT DOCUMENTS

| 6,024,575 | A | 2/2000 | Ulrich |
| 2004/0173220 | A1 | 9/2004 | Harry et al. |
| 2007/0203533 | A1* | 8/2007 | Goren et al. ............... 607/49 |
| 2010/0305478 | A1* | 12/2010 | Ordway et al. ............ 600/587 |
| 2011/0251520 | A1* | 10/2011 | Shieh et al. .............. 600/587 |

FOREIGN PATENT DOCUMENTS

EP    1880627 A1    1/2008

OTHER PUBLICATIONS

"Effect of Step-Synchronized Vibration Stimulation of Soles on Gait in Parkinson's Disease: A Pilot Study", Peter Novak et al., May 4, 2006, pp. 1-7.
International Search Report dated Jun. 21, 2012, application No. PCT/US2011/062513.

* cited by examiner

*Primary Examiner* — Anh V La
(74) *Attorney, Agent, or Firm* — RatnerPrestia

(57) ABSTRACT

Vibratory feedback systems and methods are disclosed. A vibratory feedback system includes a shoe adapted to be secured to a user's foot, a plurality of force sensors and vibration actuators mounted on the shoe, and a microprocessor affixed to the shoe. The force sensors are configured to sense forces exerted by the user's foot. The vibration actuators are configured to provide vibrations to the user's foot. The microprocessor is coupled to receive data from the plurality of force sensors, and is programmed to actuate the plurality of vibration actuators to provide a first characteristic vibration to the user's foot based on the sensed forces. A method of improving the gait of a user includes enabling the user to ambulate with the vibratory feedback system secured to the user's foot, and providing a first characteristic vibration to the user's foot based on the sensed forces using the vibratory feedback system.

18 Claims, 4 Drawing Sheets

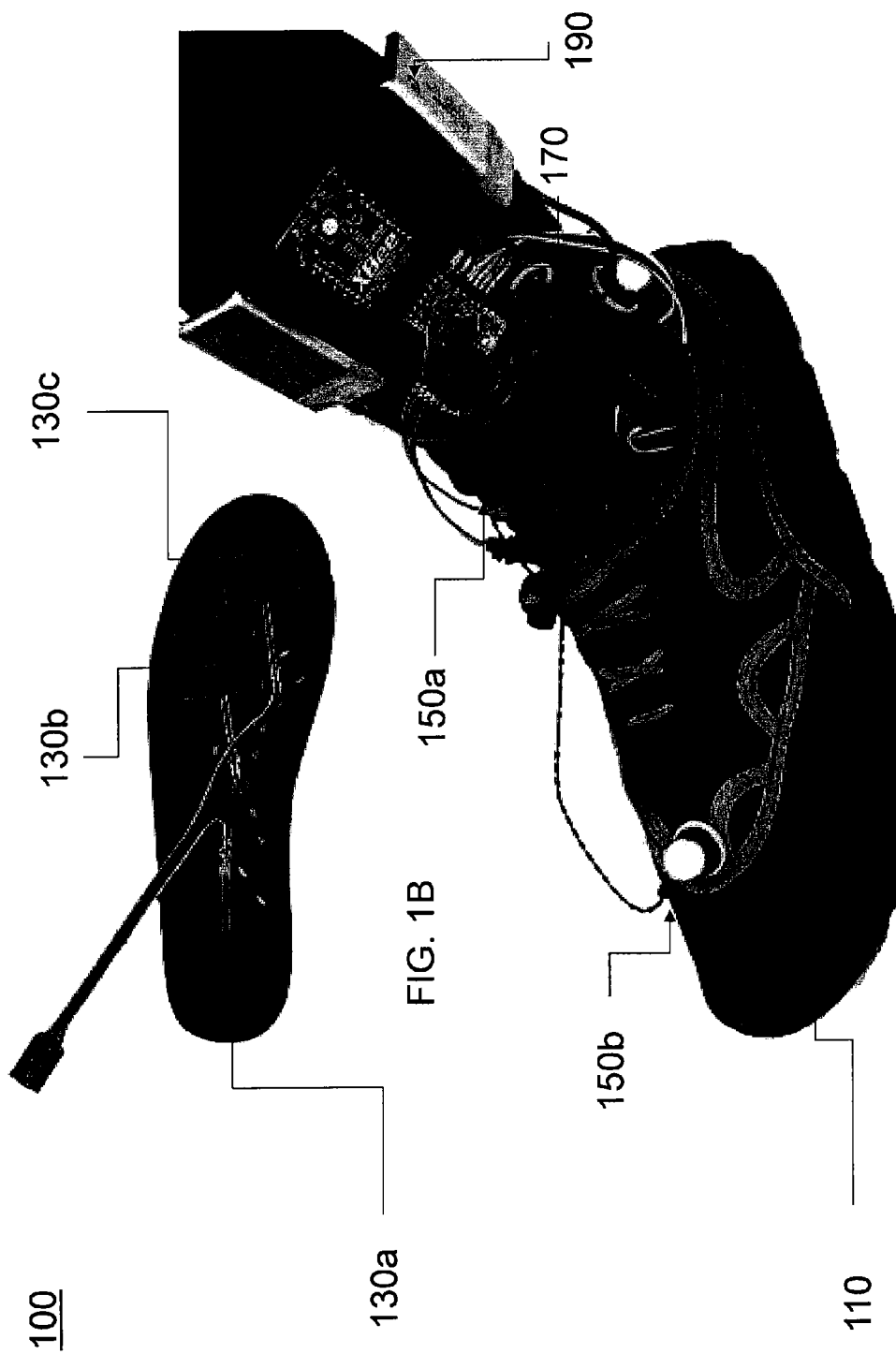

VIBRATORY FEEDBACK SYSTEMS AND METHODS

CROSS REFERENCE TO RELATED APPLICATIONS

This application claims priority to U.S. Patent Application No. 61/418,201, entitled "Shoe with Vibratory Feedback for Improving Gait of Parkinson's Patients," filed on Nov. 30, 2010, and to U.S. Patent Application No. 61/419,046, entitled "Vibratory Feedback Shoe," filed on Dec. 2, 2010, the contents of each of which are incorporated herein by reference in their entirety.

FIELD OF THE INVENTION

The present invention relates generally to vibratory feedback, and more particularly, to vibratory feedback systems and methods for improving the gait of a user.

BACKGROUND OF THE INVENTION

Often, patients with significant illnesses that affect the neurological system (e.g. Parkinson's disease) experience degradation in their control of motor skills. In particular, this degradation can significantly affect a patient's walking ability or gait. Patients with these degenerative neurological conditions may require specialized treatments to regain or maintain ambulatory ability. Accordingly, systems and methods are desired for improving the gait of patients with degenerative neurological conditions.

SUMMARY OF THE INVENTION

Aspects of the present invention relate to vibratory feedback systems and methods.

In accordance with one aspect of the present invention, a vibratory feedback system is disclosed. The vibratory feedback system comprises a shoe adapted to be secured to a foot of a user, a plurality of force sensors mounted on the shoe, a plurality of vibration actuators mounted on the shoe, and a microprocessor affixed to the shoe. The force sensors are configured to sense forces exerted by the foot of the user. The vibration actuators are configured to provide vibrations to the foot of the user. The microprocessor is coupled to receive data from the plurality of force sensors representing the sensed forces, and the microprocessor is programmed to actuate the plurality of vibration actuators to provide a first characteristic vibration to the foot of the user based on the sensed forces.

In accordance with another aspect of the present invention, a method of improving the gait of a user is disclosed. The method comprises enabling the user to ambulate with a vibratory feedback system secured to a foot of the user, and providing a first characteristic vibration to the foot of the user based on the sensed forces using the vibratory feedback system.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. This emphasizes that according to common practice, the various features of the drawings are not drawn to scale unless otherwise indicated. On the contrary, the dimensions of the various features may be expanded or reduced for clarity. Included in the drawings are the following figures:

FIGS. 1B and 1C are images of the vibratory feedback system of FIG. 1A;

DETAILED DESCRIPTION OF THE INVENTION

The systems and methods disclosed herein are usable to improve a user's gait, e.g., by developing or maintaining the user's natural walking ability. Generally, these systems and methods generate vibratory feedback for assisting the user in performing a walking motion along a desired movement path at a desired speed (trajectory). It is desirable that the walking motion be performed under the user's own power, with the vibratory feedback providing a mechanism for encouraging or discouraging particular movements performed by the user during ambulation. The systems and methods may be used while a user ambulates on a treadmill, or during a user's normal point-to-point ambulation.

The systems and methods disclosed herein are particularly suitable for users with degenerative neurological disorders (e.g., Parkinson's disease). The vibratory feedback provided by the disclosed systems and methods may be important for assisting the user in maintaining or regaining a normal, healthy gait.

Figure 1A:
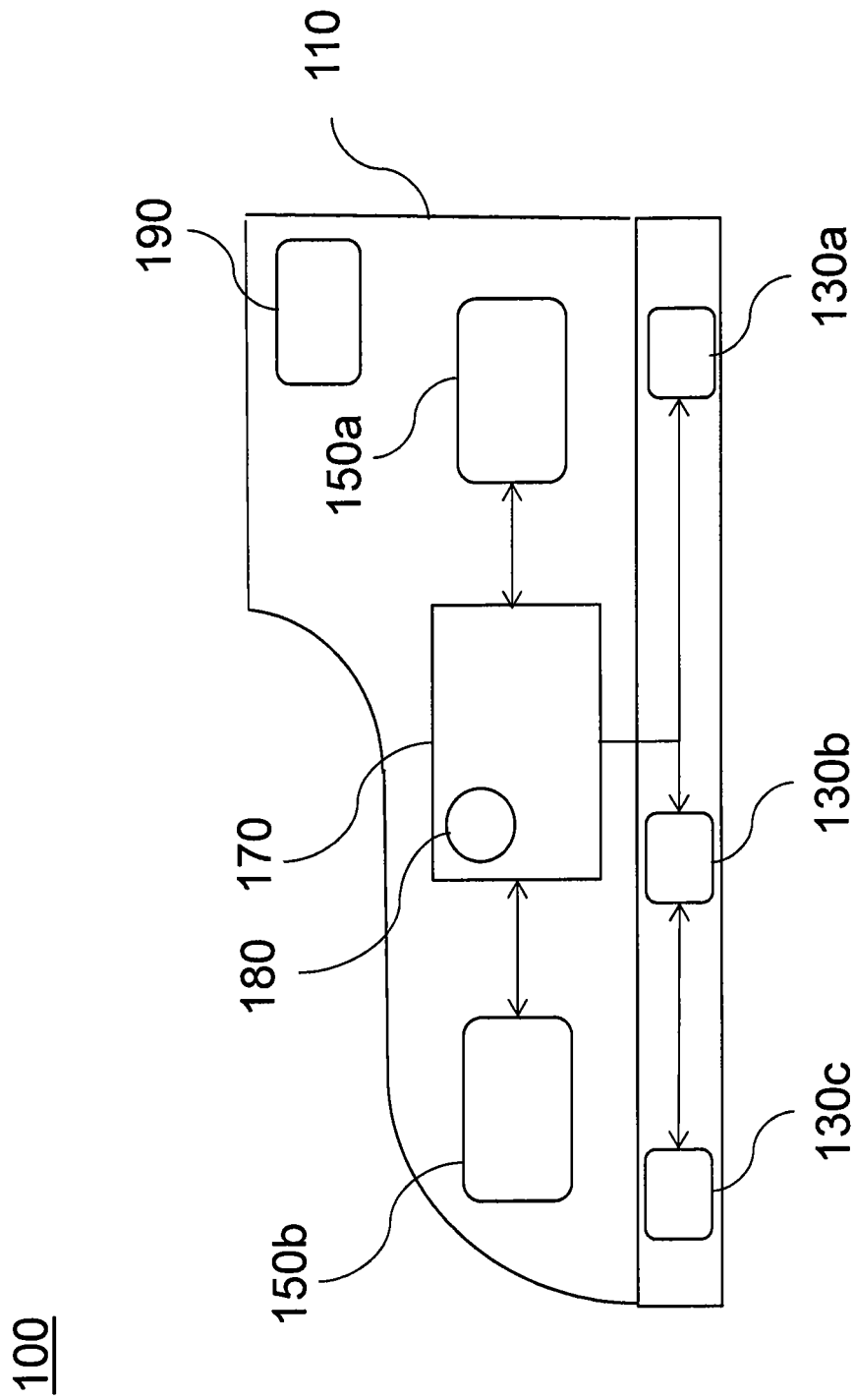
FIG. 1A is a diagram illustrating an exemplary vibratory feedback system in accordance with aspects of the present invention.

Referring now to the drawings, FIGS. 1A-1C illustrate an exemplary vibratory feedback system 100 in accordance with aspects of the present invention. Vibratory feedback system 100 is usable to improve the gait of a user. As a general overview, vibratory feedback system 100 includes a shoe 110, a plurality of force sensors 130a-130c, a plurality of vibration actuators 150a and 150b, and a microprocessor 170. Additional details of vibratory feedback system 100 are described herein.

Shoe 110 is adapted to be secured to the foot of the user of vibratory feedback system 100. As used herein, the term "shoe" is not intended to refer to any particular category or style of footwear. The term "shoe" is intended to encompass any and all structures adapted to be secured to a user's foot. Shoe 110 may desirably comprise flexible or elastic material, in order to enable use of shoe 110 by user's having different sized feet. Shoe 110 may desirably be comprised of thin, non-cushioned material in order to improve conduction of vibratory feedback to the user's foot. In an exemplary embodiment, shoe 110 comprises a water shoe. Other suitable structures for use as shoe 110 will be known to one of ordinary skill in the art from the description herein.

Force sensors 130a-130c are mounted on shoe 110. Force sensors 130a-130c are mounted on shoe 110 in positions to enable them to sense forces exerted by the user's foot during standing or ambulation by the user. In an exemplary embodiment, force sensors 130a-130c are mounted so as to be underneath the user's foot when shoe 110 is secured to the user's foot, e.g., in the sole of shoe 110.

Force sensors 130a-130c may be spaced from each other to enable sensing of forces exerted by different portions of the user's foot. In an exemplary embodiment, as shown in FIG. 1A, force sensors 130a-130c include a heel sensor 130a configured to sense a force exerted by the user's heel, a ball sensor 130b configured to sense a force exerted by the ball of the user's foot, and a toe sensor 130c configured to sense a force exerted by one or more of the user's toes. While three force sensors 130a-130c are illustrated in FIG. 1A, it will be understood that vibratory feedback system 100 may include any number of force sensors.

In an exemplary embodiment, force sensors 130a-130c are Standard 406 FSR™ force sensors provided by Interlink Electronics, of Camarillo, Calif. Other suitable sensors for use as force sensors will be known to one of ordinary skill in the art from the description herein.

Vibration actuators 150a and 150b are mounted on shoe 110. Vibration actuators 150a and 150b are mounted on shoe 110 in a configuration that enables them to provide vibrations to the user's foot. Like force sensors 130a-130c, vibration actuators 150a and 150b may be spaced from each other to enable vibrations to be provided to different portions of the user's foot. In an exemplary embodiment, as shown in FIG. 1A, rear vibration actuator 150a is mounted in a rear region of shoe 110, and front actuator 150b is mounted in a front region of shoe 110. While two vibration actuators 150a and 150b are illustrated in FIG. 1A, it will be understood that vibratory feedback system 100 may include any number of vibration actuators.

Each of the plurality of vibration actuators 150a and 150b is configured to provide a particular vibration having a controllable amplitude and frequency. Desirably, vibration actuators 150a and 150b may be configured to provide an independently controllable amplitude and frequency of vibration relative to other vibration actuators. For example, the amplitude and/or frequency of vibration for vibration actuator 150a may be selected separately and independently from that of vibration actuators 150b.

The frequency of vibrations provided by vibration actuators 150 may be selected to be in the range of frequencies that are most easily or effectively detected by the user of vibratory feedback system 100. In one preferred embodiment, vibration actuators 150a and 150b are configured to provide vibrations having a frequency in the range of approximately 200 Hz to approximately 350 Hz. This range of frequencies corresponds to the sensitivity of a group of neuroreceptors called the "Pacinian corpuscles" in the user's foot. In another preferred embodiment, vibration actuators 150 are configured to provide vibrations having a frequency in the range of approximately 3 Hz to approximately 40 Hz. This range of frequencies corresponds to the sensitivity of a group of neuroreceptors called the "Meissner's corpuscles" in the user's foot. It will be understood that these embodiments are not exclusive, and that a single vibration actuator may be configured to provide vibrations having a frequency in either of the above-described ranges, or in other frequency ranges, as would be understood by one of ordinary skill in the art. Alternatively, vibratory feedback system 100 may include a first set of vibration actuators configured to provide vibrations in one frequency range, and a second set of vibration actuators configured to provide vibrations in another frequency range, or any linear combination of any number of vibrations from any frequency range.

Vibration actuators 150a and 150b, for example, may be voice coil actuators configured to be driven using alternating current supplied from microprocessor 170. In an exemplary embodiment, vibration actuators 150a and 150b may be C-2 tactors provided by Engineering Acoustics, Inc., of Casselberry, Fla. Other suitable actuators for use as vibration actuators will be known to one of ordinary skill in the art from the description herein.

Microprocessor 170 controls the operation of vibratory feedback system 100. Microprocessor 170 is affixed to shoe 110, and is electrically coupled with force sensors 130a-130c and vibration actuators 150a and 150b. In particular, microprocessor 170 is coupled to receive data from force sensors 130a-130c representing the sensed forces. Further, microprocessor 170 is programmed to actuate vibration actuators 150a and 150b to provide a characteristic vibration to the user's foot, based on the forces sensed by force sensors 130a-130c.

In an exemplary embodiment, microprocessor 170 is a microcontroller provided by Sparkfun, Inc. of Boulder, Colo. Other suitable data processors for use as microprocessor 170 will be known to one of ordinary skill in the art from the description herein. Additional details regarding the programming of microprocessor 170, and the characteristic vibrations provided by vibratory feedback system 100, are described herein with respect to the operation of vibratory feedback system 100.

Vibratory feedback system 100 is not limited to the above components, but may include alternative or additional components, as would be understood by one of ordinary skill in the art.

Vibratory feedback system 100 may include a data storage component (not shown) for use in controlling vibratory feedback system 100, or storing data obtained during operation of vibratory feedback system 100. In an exemplary embodiment, microprocessor 170 may be configured to store data received from force sensors 130 in the data storage component, e.g., to facilitate later analysis.

Vibratory feedback system 100 may also include a wireless communication device 180, as shown in FIG. 1A. Wireless communication device 180 is operable to enable bi-directional wireless communications between microprocessor 170 and a remote monitoring unit (not shown) and/or a shoe worn on the user's other foot. In an exemplary embodiment, microprocessor 170 is programmed to transmit the data received from force sensors 130a-130c to the remote monitoring unit via wireless communication device 180. Microprocessor 170 may further be programmed to receive data for actuating vibration actuators 150a and 150b from the remote monitoring unit via wireless communication device 180. In an exemplary embodiment, wireless communication device 180 may be a wireless transducer, such as an Xbee module from Digi, Inc. of Minnetonka, Minn. Other suitable transducers for use as wireless communication device 180 will be known to one of ordinary skill in the art from the description herein.

Vibratory feedback system 100 may also include an accelerometer 190, as shown in FIG. 1A. Accelerometer 190 is mounted on shoe 110, and is configured to sense a movement of shoe 110. In an exemplary embodiment, microprocessor 170 is coupled to receive data from accelerometer 190 representing the sensed movement, and to actuate vibration actuators 150a and 150b to provide a characteristic vibration to the user's foot, based on the movement of shoe 110 sensed by accelerometer 190. Suitable sensors for use as accelerometer 190 include, for example, the ADXL-335 accelerometer, provided by Analog Devices, of Norwood, Mass. Other suitable accelerometers for use as accelerometer 190 will be known to one of ordinary skill in the art from the description herein.

The operation of vibratory feedback system 100 will now be described in accordance with aspects of the present invention. In operation, a user secures vibratory feedback system 100 to his or her foot, and ambulates under his or her own power. During ambulation, the user's foot naturally exerts a force on the surface being walked upon. Force sensors 130a-130c sense the force exerted by the user's foot, and transmit data representing the sensed forces to microprocessor 170 for analysis.

As set forth above, microprocessor 170 is programmed to actuate the plurality of vibration actuators 150a and 150b to provide a characteristic vibration based on the forces sensed by force sensors 130a-130c. In particular, microprocessor 170 may be operable to provide multiple characteristic vibrations based on the particular forces sensed by force sensors 130a-130c. As used herein, the term "characteristic vibration" refers to a specific vibration profile having specific amplitude and frequency characteristics felt by the user's foot due to actuation of vibration actuators 150a and 150b by microprocessor 170.

Microprocessor 170 selects the characteristic vibration to be provided based on the forces sensed by force sensors 130a-130c. For example, microprocessor 170 is programmed to actuate vibration actuators 150a and 150b to provide a first characteristic vibration when the sensed forces satisfy a first set of conditions, and a second characteristic vibration different in amplitude, frequency, and/or location of the actuators used when the sensed forces satisfy a second set of conditions.

Figure 2:
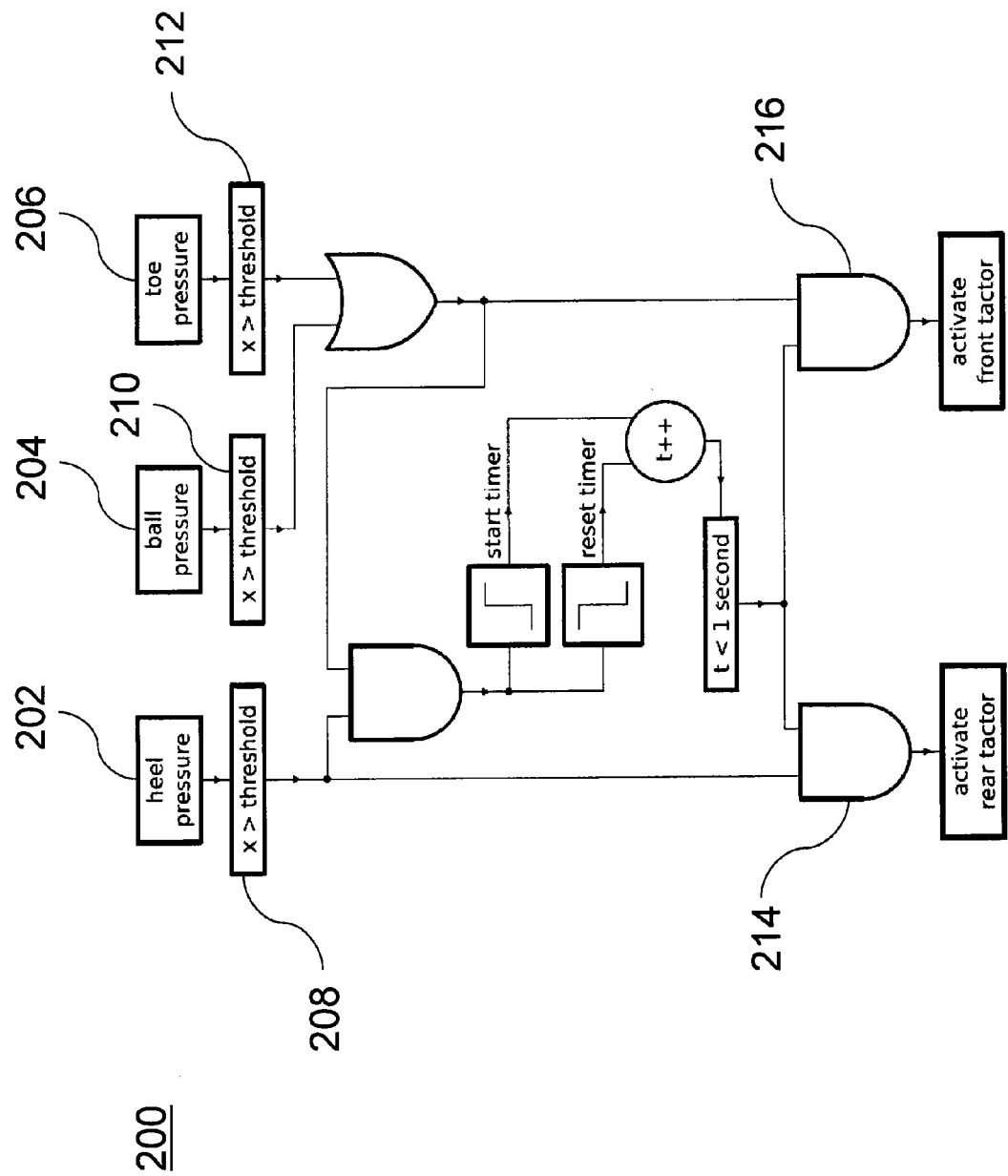
FIG. 2 is a logic diagram illustrating an exemplary operation of the vibratory feedback system of FIG. 1A.

FIG. 2 is a logic diagram 200 illustrating an exemplary operation of vibratory feedback system 100. During ambulation by the user, heel sensor 130a senses a force 202 exerted by the user's heel, ball sensor 130b senses a force 204 exerted by the ball of the user's foot, and toe sensor 130c senses a force 206 exerted by the user's toe(s). Each of these forces 202, 204, and 206 has an associated predetermined threshold 208, 210, and 212, such as, for example, a threshold of approximately one pound. As illustrated in FIG. 2, vibration actuators 150a and 150b each have an associated logic gate 214 and 216 for controlling whether the respective actuator is to be actuated.

When (i) force 202 exceeds threshold 208, and (ii) forces 204 and 206 do not exceed thresholds 210 and 212 (i.e. gate 214 is open, and gate 216 is closed), then microprocessor 170 controls rear actuator 150a to provide a first characteristic vibration (i.e. vibrate at a predetermined amplitude and frequency). The frequency may be in the range of approximately 200 Hz to approximately 350 Hz, and more preferably, may be approximately 237 Hz. This first condition may be satisfied by a heel strike during ambulation.

When (i) either force 204 or 206 exceeds its respective threshold 210 or 212, and (ii) force 202 does not exceed threshold 208 (i.e., gate 214 is closed, and gate 216 is opened), then microprocessor 170 controls front actuator 150b to provide a second characteristic vibration. The frequency may be in the range of approximately 200 Hz to approximately 350 Hz, and more preferably, may be approximately 237 Hz. This second condition may be satisfied during the push-off phase of ambulation.

When (i) force 202 exceeds threshold 208, and (ii) either force 204 or 206 exceeds its respective threshold 210 or 212 (i.e. gates 214 and 216 are opened), then microprocessor 170 controls both rear actuator 150a and front actuator 150b to provide a third characteristic vibration. Both vibration actuators 150 may vibrate with a frequency in the range of approximately 3 Hz to approximately 40 Hz, and more preferably, may be approximately 20 Hz. This third condition may be satisfied during the stance phase of ambulation.

It may be desirable to terminate the vibration when the user is no longer walking. Thus, when above-described third condition has been satisfied for a predetermined length of time (e.g., one second), then microprocessor controls vibration actuators 150a and 150b to stop providing the third characteristic vibration (i.e. close gates 214 and 216).

Figure 3:
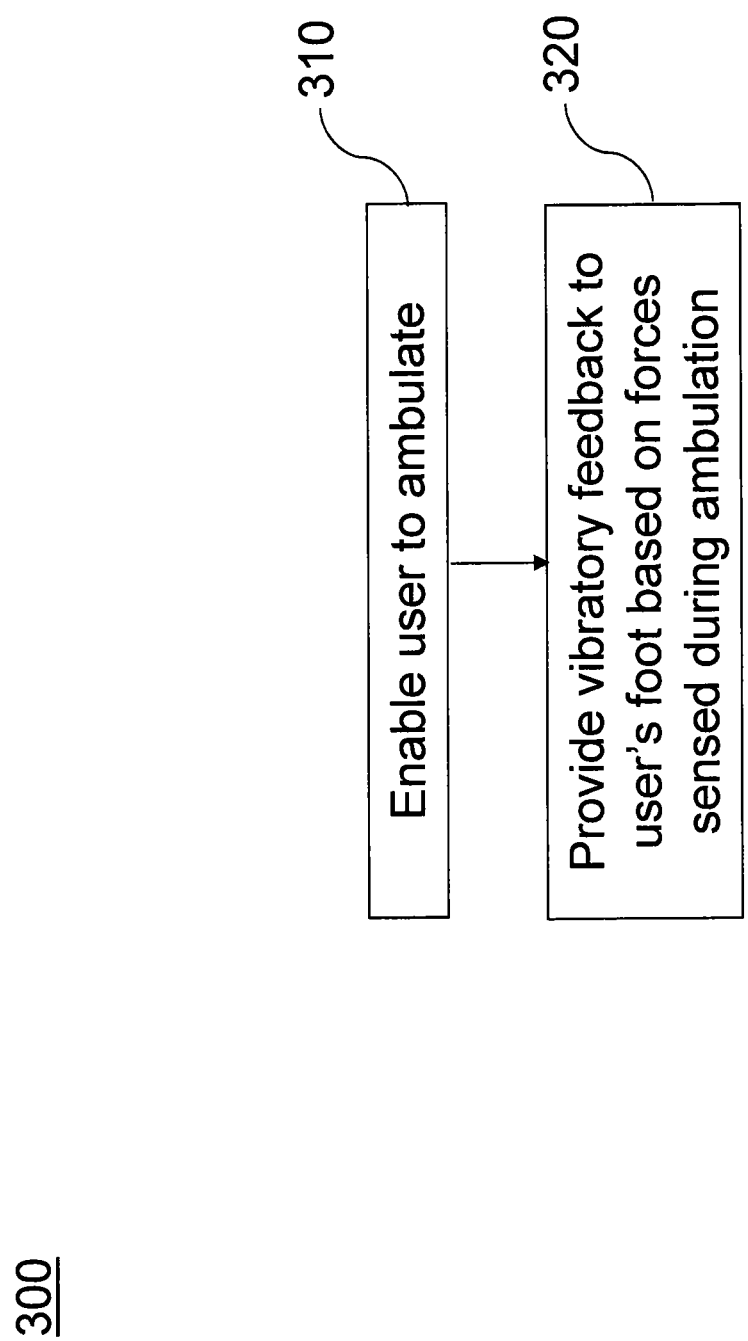
FIG. 3 is a flow chart illustrating an exemplary method for improving the gait of a user in accordance with aspects of the present invention.

FIG. 3 shows an exemplary method for improving the gait of a user 300 in accordance with aspects of the present invention. As a general overview, method 300 includes enabling a user to ambulate and providing a characteristic vibration to the user's foot. Additional details of method 300 are described herein with respect to the components of vibratory feedback system 100.

In step 310, a user is enabled to ambulate. In an exemplary embodiment, a user is enabled to ambulate with vibratory feedback system 100 secured to the user's foot. Vibratory feedback system 100 includes a plurality of force sensors 130a-130c configured to sense forces exerted by the user's foot during step 310.

In step 320, a characteristic vibration is provided to the user's foot. In an exemplary embodiment, microprocessor 170 provides a characteristic vibration to the user's foot by operating vibration actuators 150a and 150b based on the forces sensed by force sensors 130a-130c.

Microprocessor 170 selects the characteristic vibration to be provided based on the forces sensed by force sensors 130a-130c. For example, microprocessor 170 is programmed to actuate vibration actuators 150a and 150b to provide a first characteristic vibration when the sensed forces satisfy a first set of conditions, and a second characteristic vibration different in amplitude and/or frequency when the sensed forces satisfy a second set of conditions. Microprocessor 170 may provide any of the characteristic vibrations (based on any of the conditions) described above with respect to the operation of vibratory feedback system 100.

Method 300 is not limited to the above steps, but may include alternative steps and additional steps, as would be understood by one of ordinary skill in the art from the description herein.

For one example, when system 100 includes a data storage component, method 300 may comprise the step of storing the data received from force sensors 130a-130c. In an exemplary embodiment, microprocessor 170 stores data received from force sensors 130a-130c in the data storage component, e.g., to facilitate later analysis.

For another example, when system 100 includes wireless communication device 180, method 300 may comprise transmitting the data received from force sensors 130a-130c to a remote monitoring unit. In an exemplary embodiment, microprocessor 170 transmits the data received from force sensors 130a-130c to the remote monitoring unit via wireless communication device 180. Microprocessor 170 may further receive data for actuating vibration actuators 150a and 150b from the remote monitoring unit via wireless communication device 180.

For yet another example, it may be desirable to optimize the characteristic vibration provided by vibratory feedback system 100. Accordingly, method 300 may include monitoring the forces sensed by force sensors 130a-130c during ambulation by the user during step 310, and modifying the characteristic vibration provided during step 320 in amplitude or frequency, to create a modified characteristic vibration. These monitoring and modifying steps may be repeated in order to effect a change in the forces exerted by the user (and sensed by force sensors 130a-130c). When the forces exerted by the user substantially match desired forces, and/or the user's gait substantially matches a desired (or improved) gait, the characteristic vibration may correspond to an optimal characteristic vibration for the user. This optimal characteristic vibration may then be used to provide the vibratory feedback in step 320.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A vibratory feedback system comprising:
a shoe adapted to be secured to a foot of a user;
a plurality of force sensors mounted on the shoe, the force sensors configured to sense forces exerted by the foot of the user, the plurality of force sensors comprising at least:
 a heel sensor configured to sense a force exerted by a heel of the foot of the user; and
 one of:
  a ball sensor configured to sense a force exerted by a ball of the foot of the user, or
  a toe sensor configured to sense a force exerted by one or more toes of the foot of the user;
a plurality of vibration actuators mounted on the shoe, the vibration actuators configured to provide vibrations to the foot of the user; and
a microprocessor affixed to the shoe, the microprocessor coupled to receive data from the plurality of force sensors representing the sensed forces, and the microprocessor programmed to actuate the plurality of vibration actuators to provide (a) a first characteristic vibration to the foot of the user when a sensed force from the heel sensor satisfies a first condition, and (b) a second characteristic vibration different in amplitude, frequency, or location from the first characteristic vibration when a sensed force from the one of the ball sensor or toe sensor satisfies a second condition.

2. The vibratory feedback system of claim 1, wherein the plurality of force sensors further comprise:
both the ball sensor and the toe sensor.

3. The vibratory feedback system of claim 1, wherein the plurality of vibration actuators comprise at least:
a front actuator mounted in a front region of the shoe; and
a rear actuator mounted in a rear region of the shoe.

4. The vibratory feedback system of claim 1, wherein each of the plurality of vibration actuators has an independently controllable amplitude and frequency of vibration relative to other of the plurality of vibration actuators.

5. The vibratory feedback system of claim 1, wherein the vibration actuators are configured to provide vibrations having a frequency in the range of approximately 200 Hz to approximately 350 Hz.

6. The vibratory feedback system of claim 1, wherein the vibration actuators are configured to provide vibrations having a frequency in the range of approximately 3 Hz to approximately 40 Hz.

7. The vibratory feedback system of claim 1, wherein
the first condition comprises a force exerted by the user's heel in excess of a first predetermined threshold;
the first characteristic vibration comprises a vibration provided to the user's heel;
the second condition comprises a force exerted by the user's toes or the ball of the user's foot in excess of a second predetermined threshold; and
the second characteristic vibration comprises a vibration provided to the user's toes or the ball of the user's foot.

8. The vibratory feedback system of claim 1, wherein the microprocessor is configured to store the data received from the plurality of force sensors for later analysis.

9. The vibratory feedback system of claim 1, further comprising:
a wireless communication device,
wherein the microprocessor is programmed to transmit the data received from the plurality of force sensors to a remote monitoring unit via the wireless communication device.

10. The vibratory feedback system of claim 9, wherein the microprocessor is programmed to receive data for actuating the plurality of vibration actuators from the remote monitoring unit via the wireless communication device.

11. The vibratory feedback system of claim 1, further comprising:
an accelerometer mounted on the shoe, the accelerometer configured to sense a movement of the shoe,
wherein the microprocessor is coupled to receive data from the accelerometer representing the movement of the shoe, and the microprocessor coupled to actuate the plurality of vibration actuators based on the movement of the shoe.

12. A method of improving the gait of a user comprising the steps of:
enabling the user to ambulate with a vibratory feedback system secured to a foot of the user, the vibratory feedback system comprising a plurality of force sensors configured to sense forces exerted by the foot of the user, the plurality of force sensors comprising at least a heel sensor and one of a ball sensor or a toe sensor;
sensing a force exerted by a heel of the foot of the user during the ambulation using the heel sensor;
sensing a force exerted by a ball of the foot of the user or a force exerted by one or more toes of the foot of the user during the ambulation using the one of the ball sensor or the toe sensor;
providing a first characteristic vibration to the foot of the user when a sensed force from the heel sensor satisfies a first condition, and
providing a second characteristic vibration to the foot of the user different in amplitude, frequency, or location from the first characteristic vibration when a sensed force from the one of the ball sensor or toe sensor satisfies a second condition.

13. The method of claim 12, wherein
the first condition comprises a force exerted by the user's heel in excess of a first predetermined threshold;
the first characteristic vibration comprises a vibration provided to the user's heel;
the second condition comprises a force exerted by the user's toes or the ball of the user's foot in excess of a second predetermined threshold; and
the second characteristic vibration comprises a vibration provided to the user's toes or the ball of the user's foot.

14. The method of claim 12, further comprising the steps of:
monitoring the forces sensed by the plurality of force sensors during the ambulation by the user; and
modifying the first characteristic vibration in amplitude and/or frequency to create a modified characteristic vibration.

15. The method of claim 14, further comprising repeating the monitoring and modifying steps until an optimal characteristic vibration is created.

16. The method of claim 12, further comprising the step of:
storing the data received from the plurality of force sensors for later analysis.

17. The method of claim 12, further comprising the step of:
transmitting the data received from the plurality of force sensors to a remote monitoring unit via a wireless communication device.

18. The method of claim 17, further comprising the step of:
receiving data for providing the first characteristic vibration from the remote monitoring unit via the wireless communication device.

* * * * *